United States Patent
Ahting et al.

(10) Patent No.: US 6,867,337 B2
(45) Date of Patent: Mar. 15, 2005

(54) PROCESS FOR PRODUCING GLYCERIN

(75) Inventors: Herbert C. Ahting, Cincinnati, OH (US); David A. Krabacher, Fairfield, OH (US)

(73) Assignee: Cognis Corporation, Ambler, PA (US)

( * ) Notice: Subject to any disclaimer, the term of this patent is extended or adjusted under 35 U.S.C. 154(b) by 25 days.

(21) Appl. No.: 10/668,978

(22) Filed: Sep. 23, 2003

(65) Prior Publication Data

US 2004/0059164 A1 Mar. 25, 2004

Related U.S. Application Data

(63) Continuation of application No. 10/185,464, filed on Jun. 27, 2002.
(60) Provisional application No. 60/309,250, filed on Jul. 31, 2001.

(51) Int. Cl.$^7$ .......................... C07C 27/00; C07C 27/02; C07C 31/18; C07C 27/26; C07C 29/74
(52) U.S. Cl. ....................... 568/858; 568/840; 568/852; 568/869; 422/1
(58) Field of Search ................................ 568/858, 840, 568/852, 869; 422/1

(56) References Cited

PUBLICATIONS

Twenty–Second Commission Directive 98/16/EC, Mar. 5, 1998, Official Journal of the European Communities, L 77/44 through L 77/46.

Twenty–Fourth Commission Directive 2000/6/EC, Feb. 29, 2000, Official Journal of the European Communities, L 56/42 through L 56/46.

*Primary Examiner*—Elvis O. Price
(74) *Attorney, Agent, or Firm*—Aaron R. Ettelman

(57) ABSTRACT

A process for producing glycerin is comprised of the steps of: (1) contacting a fat with water at a temperature and pressure sufficient to produce hydrolyzed fat and a sweet water stream comprised of water, fat and glycerin; (2) introducing the sweet water stream into a vertical constant temperature zone and heating the sweet water stream to a temperature of at least 200° C.; (3) allowing sweet water stream of step (2) to separate into a top layer comprised of fat and a bottom layer comprised of glycerin and water while maintaining a temperature of the two layers of at least about 200° C. for a period of time sufficient to deactivate the prions; (4) separating the glycerin from the water.

7 Claims, 1 Drawing Sheet

Heat Treatment Reactor

US 6,867,337 B2

PROCESS FOR PRODUCING GLYCERIN

CROSS-REFERENCE TO RELATED APPLICATIONS

This application claims the benefit of copending application Ser. No. 10,185,464, filed Jun. 27, 2002, which application claims the benefit of provisional application Ser. No. 60/309,250, filed on Jul. 31, 2001, the entire contents of each application is incorporated herein by reference.

STATEMENT REGARDING FEDERALLY SPONSORED RESEARCH OR DEVELOPMENT

Not applicable.

BACKGROUND OF THE INVENTION

Tallow, which is animal fat derived from the rendering of cattle and other sources such as sheep, is a primary feedstock for the production of fatty acids and glycerin. A hydrolysis reactor, also known as a "splitter" in the fatty acid industry, is used to hydrolyze fat into fatty acid and glycerin. These reactors operate at conditions exceeding the requirement of the regulations to produce heated treated fatty acids. The tallow is fed into the lower part of the splitter. Conversion of fat to fatty acids occurs as this material moves up through the reactor column. The fatty acids are removed from the top of the reactor column. Due to the design of these splitters, the fat feed that enters near the bottom, contacts and cools the sweet water (dilute glycerin) that flows to the bottom. The sweet water along with some entrained and untreated fat are then removed from the bottom of splitter. This process is described in U.S. Pat. No. 2,156,863, the entire contents of which are incorporated herein by reference.

Prions are small, proteinaceous infectious particles that resist inactivation by procedures which affect nucleic acids. Prions, which is an acronym that stands for "proteinaceous infectious particle", are generally believed to be the causative agents for a family of diseases known as "transmissible spongiform encephalopathy" (TSE). Prions are composed largely, if not entirely, of a protein designated as the scrapie isoform of the prion protein, PrPSc.

BSE (bovine transmissible spongiform encephalopathy) is the cow version of TSE, popularly known as mad cow disease. In humans the disease as transmitted from cows is called variant or new variant Creutzfeldt-Jakob Disease (vCJd or nvCJD). Some researchers believe that the prions are DNA-free and RNA-free protein particles which either self-replicate, or induce replication by interaction with normal proteins, in the nervous systems of various mammals and ultimately cause the formation of deposits/platelets in the brain which leads to dementia-like symptoms and death.

Glycerin that is produced from fat from cows having mad cow disease can be contaminated with prions. This problem has been especially acute in Europe where mad cow disease has been prevalent in the past few years. European governmental health regulating authorities have prescribed conditions under which it is believed that the prions can be sufficiently treated so as to limit the spread of mad cow disease. These conditions are set forth in two European Union directives—the Twenty-second Commission Directive 98/16/EC of Mar. 5, 1998 and Twenty-fourth Commission Directive 2000/6EC of Feb. 29, 2000 relating to cosmetic products. One of the prescribed treatments requires exposure of the potentially contaminated material, such as glycerin produced from the splitting of prion-contained tallow, to conditions of at least 200° C. (392° F.) for a minimum of 20 minutes, under appropriate pressure, and in the presence of water.

Because glycerin and water from a fat splitting process can be contaminated with prions, there is a need for a reliable process that will produce glycerin and water containing only deactivated prions.

BRIEF SUMMARY OF THE INVENTION

The present invention pertains to a method for producing glycerin comprising the steps of (1) contacting a prion-contaminated fat with water at a temperature and pressure sufficient to produce hydrolyzed fat and a sweet water stream comprised of water, fat and glycerin; (2) introducing the sweet water stream into a vertical constant temperature zone and heating the sweet water stream under pressure to a temperature of at least 200° C.; (3) allowing the sweet water stream of step (2) to separate into a top layer comprised of fat and a bottom layer comprised of glycerin and water while maintaining a temperature of the two layers of at least about 200° C. under pressure for a period of time sufficient to substantially deactivate the prions; (4) separating the glycerin from the water.

The process according to the invention produces glycerin and water both of which contain deactivated prions from glycerin and water derived from the splitting of fat potentially contaminated with prions. The process according to the invention is comprised of a heat treatment operation that deactivates prions inserted between the steps of fat hydrolysis and glycerin recovery and treatment in a conventional glycerin manufacturing operation.

The process according to the invention produces glycerin products that meet regulatory derived customer requirements in so far as active prion content is concerned. The heat treatment steps and their placement within an overall glycerin production operation, not only affect the glycerin portion of the sweet water but also the water portion and allow the water to be recycled into the splitting process without introducing additional active prion contamination. Accordingly, one advantage of the process according to the invention is that it ensures that the water portion of the sweet water, which is typically recovered by later evaporation of a glycerin-water stream, is ideally suited for reuse in the splitter. Water, needed for fat hydrolysis, is recycled to the top of the splitter, where it contacts the already treated fatty acid that is about to exit the splitter. Another advantage of the process according to the invention is its ability to separate and remove the entrained fat from the sweet water as described in more detail below thereby preventing fouling of heat exchange surfaces employed in the evaporation of water from glycerin.

Another aspect of the invention is a process for deactivating prions in an aqueous glycerine mixture comprising the steps of (1) providing an aqueous mixture comprising glycerin wherein the glycerin is contaminated with prions; (2) heating the aqueous mixture to a temperature of at least about 200° C. under pressure for a period of time sufficient to substantially deactivate the prions.

DETAILED DESCRIPTION OF THE INVENTION

Figure 1:
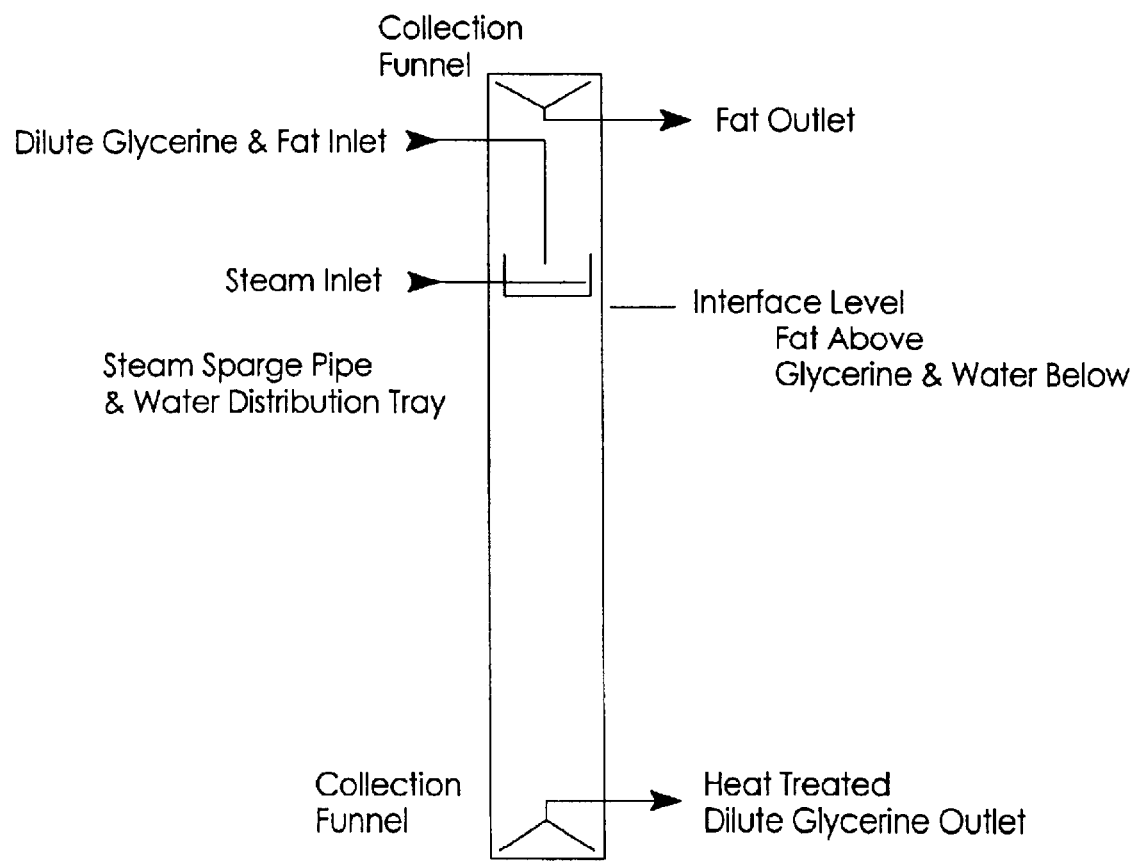
FIG. 1 depicts the configuration of a process vessel used to heat the dilute glycerin, provide hold-up time for that material within a pressure containment vessel and allow for separation of entrained fat.

In the process according to the invention, sweet water containing fat derived from the splitter is heated by any means that will increase the temperature to at least 200° C. under pressure and maintain the temperature for a time period sufficient to substantially deactivate the prions. Typically, this time period will be about at least 20 minutes. This heat treatment could be effected in a number of ways such as, for example, by means of an external heat exchanger on the feed stream that could heat the glycerin to at least 200° C. prior to the stream's entry into the vertical constant temperature zone. Such a heat exchanger could be supplied with energy from indirect contact with steam or heat transfer fluid. The heat treatment could also be effected by direct contact with steam inside or outside of the vertical constant temperature zone vessel.

The heated sweet water stream is then maintained in a constant temperature zone at a temperature and pressure and for a time period sufficient to substantially deactivate the prions present in the sweet water. The prions are substantially deactivated when they can no longer cause transmissible spongiform encephalopathy in animals including humans. The constant temperature zone can be enclosed in any type of vertical container such as a column or other type of cylindrical vessel, preferably a vertical column capable of withstanding pressures equal to at least the autogenous pressure of water at the elevated temperatures required for prion deactivation. Because there is normally unhydrolyzed fat present in the sweet water, an interface between fat and sweet water is formed and maintained within the constant temperature zone. The position of the fat/glycerin-water interface is maintained to allow the glycerin-water phase to be maintained at a temperature of at least 200° C. and at an elevated pressure for a period to substantially deactivate the prions. Typically, this time period will be about at least 20 minutes. When the constant temperature zone is contained within a vertical column, the vertical location of the interface is stabilized by controlling the removal rate of any fat from the top of reactor and sweet water removal rate from the bottom of the reactor.

An elevated pressure is maintained in the constant temperature zone in order to prevent undesired mixing of the fat/sweet water caused by boiling and to allow the water to reach an elevated temperature such as 200° C. Based on the physical properties of water at 392° F. (200° C.), a pressure of at least 211 psig is required. When steam is added directly to this process for heating, steam must be available at a pressure greater than the reactor operating pressure. In practice, a temperature greater than the 392° F. and at an autogenous pressure developed thereby must be maintained inside the reactor column. Typically, the operating conditions will be a pressure up to about 300 psig and a temperature of up to about 422° F. Greater pressures and temperatures would similarly accomplish the desired results, but may have economic drawbacks by requiring the use of potentially more expensive pressure equipment and higher energy consumption.

While any type of animal-derived fat (tallow) can be used in the process according to the invention, it is particularly useful for deactivating prions in tallow from which SRM (specific or specified risk materials) have not been removed. SRMs are tissues and organs associated with the spinal cord and nervous system and certain other organs of animals exposed to TSE in general or BSE in particular.

The degree of deactivation of prions can be determined by methods described by Thomas Raul Appel et al. in the Journal of General Virology (2001), 82, 465–473, the entire contents of which are incorporated herein by reference.

EXAMPLE

The sweet water stream (dilute glycerin+fat) from a fat splitter was fed to a vertical heat treatment pressure reactor as shown in FIG. 1. The feed stream was contacted with steam and the feed stream and steam were mixed in the vicinity of a distribution tray near the top of vessel. The temperature of the heated feed stream was about 392° F. (200° C.). An interface formed below the steam inlet. The interface separated a top fat layer from the bottom water/glycerin layer. The water/glycerin layer was removed at the bottom of the vessel and the fat layer was removed at the top of the vessel at such a rate as to provide a residence time for the water/glycerin layer to be at least 20 minutes. The vessel was operated under a pressure of from about 211 to about 230 psig.

What is claimed is:

1. A method for producing glycerin comprising the steps of (1) contacting a prion-contaminated fat with water at a temperature and pressure sufficient to produce hydrolyzed fat and a sweet water stream comprised of water, fat and glycerin; (2) introducing the sweet water stream into a vertical constant temperature zone and heating the sweet water stream under pressure to a temperature of at least 200° C.; (3) allowing the sweet water stream of step (2) to separate into a top layer comprised of fat and a bottom layer comprised of glycerin and water while maintaining a temperature of the two layers of at least about 200° C. under pressure for a period of time sufficient to substantially deactivate the prions; (4) separating the glycerin from the water.

2. The method of claim 1 wherein the prion-contaminated fat is beef tallow.

3. The method of claim 1 wherein the vertical constant temperature zone is a vertical column.

4. The method of claim 1 wherein the pressure in steps (2) and (3) is up to about 300 psig.

5. The method of claim 1 wherein the temperature in steps (2) and (3) is up to about 422° F.

6. The method of claim 1 wherein the period of time in steps (2) and (3) is at least 20 minutes.

7. A method for producing glycerin comprising the steps of (1) contacting a prion-contaminated beef tallow with water at a temperature and pressure sufficient to produce hydrolyzed fat and a sweet water stream comprised of water, fat and glycerin; (2) introducing the sweet water stream into a vertical column and heating the sweet water stream to a temperature of about 422° F. and under pressure of about 300 psig; (3) allowing the sweet water stream of step (2) to separate into a top layer comprised of fat and a bottom layer comprised of glycerin and water while maintaining a temperature of about 422° F. and a pressure of about 300 psig for at least 20 minutes to substantially deactivate the prions; (4) separating the glycerin from the water.

* * * * *